US00PP24879P3

(12) United States Plant Patent
Cain

(10) Patent No.: US PP24,879 P3
(45) Date of Patent: Sep. 16, 2014

(54) GRAPEVINE 'IFG TWELVE'

(50) Latin Name: ***Vitis interspecific* hybrid**
Varietal Denomination: IFG Twelve

(75) Inventor: David Cain, Bakersfield, CA (US)

(73) Assignee: International Fruit Genetics, LLC, Bakersfield, CA (US)

( * ) Notice: Subject to any disclaimer, the term of this patent is extended or adjusted under 35 U.S.C. 154(b) by 95 days.

(21) Appl. No.: 13/507,543

(22) Filed: Jul. 9, 2012

(65) Prior Publication Data

US 2014/0013474 P1 Jan. 9, 2014

(51) Int. Cl.
*A01H 5/00* (2006.01)

(52) U.S. Cl.
USPC ..... Plt./205

(58) Field of Classification Search
USPC ..... Plt./205
See application file for complete search history.

*Primary Examiner* — Annette Para

(57) ABSTRACT

This invention is a new and distinct grapevine variety denominated 'IFG Twelve'. The new grapevine is characterized by producing very pointed narrow reddish purple grapes having small to medium sized seed traces.

1 Drawing Sheet

Latin name of the genus and species claimed: *Vitis* interspecific hybrid.

Variety denomination: 'IFG Twelve'.

BACKGROUND OF THE INVENTION

The new and distinct grapevine described and claimed herein originated from a hand pollinated cross of the Calinda variety and A2409 an unnamed interspecific very elongate pointed seedless grape selection from the University of Arkansas breeding program hybridized in May 2002. The abortive seed traces were subsequently embryo cultured and the resulting plant was planted in the field in April 2003. The present variety of grapevine was selected as a single plant in July 2004 and was first asexually propagated by hardwood cuttings in December 2004, near Delano, Kern County, Calif. The resulting propagules were planted during April 2005 near Delano, Kern County, Calif. and were found to reproduce true-to-type through at least two generations of asexual reproduction.

BRIEF SUMMARY OF THE INVENTION

The new grapevine 'IFG Twelve' is characterized by producing extremely narrow elongated seedless fruit with a characteristic pointed tip. The shape, which to the author's knowledge is unique among commercially available seedless table grape varieties, provides consumers with a distinct visual signal to identify the new variety. The new variety is further characterized by producing medium firm reddish black fruits which ripen early in the growing season. Berries are moderately crisp in texture, mild flavored and may have small to medium size rudimentary seed traces. Bunches are long with narrow shoulders and are naturally loose so require no gibberellin for berry thinning. Vines of 'IFG Twelve' are moderately productive and may require cane pruning. The fruit ripen early season usually mid to late July in Delano.

'IFG Twelve' differs from its maternal parent by producing very elongated narrow pointed reddish black berries having small to medium seed traces as opposed to the red elongated fruits having very large seed traces of the Calinda variety. It differs from its pollen parent by possessing more firm berries with reddish black coloration as opposed to the narrow, elongate pointed black fruits of A2409. The skin of 'IFG Twelve' is thinner and the taste is less herbaceous than the A2409.

BRIEF DESCRIPTION OF THE FIGURE

The accompanying photographic illustration in FIG. 1 illustrates in full color 'IFG Twelve'. The photograph was taken outdoors with indirect lighting. The colors are as nearly true as is reasonably possible in a color representation of this type.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*vitis* spp.) (1983) which was developed in collaboration with the Office International de la Vigne et du Vin (OIV) and the International Union for the Protection of New Varieties of Plants (UPOV).

The descriptive matter which follows pertains to 'IFG Twelve' plants grown in the vicinity of Delano, Kern County, Calif. during 2009 and 2010, and is believed to apply to plants of the variety grown under similar conditions of soil and climate elsewhere:

VINE

General:
*Size*.—Large.
*Vigor*.—Vigorous.
*Density of foliage*.—Dense.
*Productivity*.—Productive.
*Root stock*.—Own root.
*Training method*.—Typically spur pruned leaving 2 bud spurs.

Trunk:
*Trunk diameter of 6-year-old vines at 30 cm above the soil line*.—13.1 cm.
*Shape*.—Stocky.
*Straps*.—Very long.
*Surface texture*.—Shaggy.
*Inner bark color*.—Can be any of the following colors; Grey brown; N199B, and Greyed orange; 165A.

SHOOTS

Young shoot:
*Form of tip*.—Wide open.
*Distribution of anthocyanin coloration of tip*.—Piping (striped).
*Intensity of anthocyanin coloration of tip*.—Weak to Medium.
*Density of prostrate hairs of tip*.—Sparse.
*Density of erect hairs of tip*.—Absent.
*Color*.—Can be any of the following colors; Yellow-green; N144C, and 144B.

Woody shoot (mature canes):
*Shape*.—Stocky.
*Internode length*.—Medium; About 10.3 cm.
*Width at node*.—About 0.8 cm.
*Cross section*.—Circular.
*Surface*.—Striate.
*Main color*.—Can be any of the following colors; Greyed-orange; 166A, and B, and C, and 165A, and 174A.
*Density of erect hairs of nodes*.—None or very sparse.
*Density of erect hairs on internodes*.—None or very sparse.
*Growth of axillary shoots*.—Strong; Approximately 44.3 cm.

Flowering shoot:
*Vigor during flowering*.—Strong.
*Attitude during flowering on shoots not tied*.—Semi-erect.
*Color*.—Dorsal side of internodes — Green with Red stripes.
*Color*.—Ventral side of internodes — Green.
*Color*.—Dorsal side of nodes — Green.
*Color*.—Ventral side of nodes — Green.
*Density of prostrate hairs of nodes*.—None — Very sparse.
*Density of erect hairs of nodes*.—None.
*Density of prostrate hairs on internode*.—None.
*Density of erect hairs on internode*.—None.
*Anthocyanin coloration of buds*.—Absent.

Tendrils:
*Distribution on the shoot (at full flowering)*.—Discontinuous.
*Length of tendril*.—Long; About 24.0 cm.
*Thickness*.—Medium.
*Color*.—Can be any of the following colors; N144A, and B, with Greyed-orange at tip of new growth; 164A.
*Form*.—Bifurcated to trifurcated.
*Number of consecutive tendrils*.—2.

LEAVES

Young leaves:
*Color of upper surface of first four distal unfolded leaves*.—Green with bronze spots.
*Average intensity of anthocyanin coloration of six distal leaves prior to flowering*.—Absent or very weak.
*Density of prostrate hairs between veins (lower surface)*.—Absent.
*Density of prostrate hairs on veins (lower surface)*.—Absent — very sparse.
*Density of erect hairs between veins (lower surface)*.—Absent.
*Density of erect hairs on veins (lower surface)*.—Sparse.

Mature leaves:
*Average length*.—About 16.2 cm.
*Average width*.—About 14.8 cm.
*Mature leaf size*.—Medium large.
*Shape of blade*.—Wedge-shaped.
*Number of lobes*.—5.
*Anthocyanin coloration of main veins on upper side of blade*.—Very weak.
*Mature leaf profile*.—V-shaped to undulate.
*Blistering surface of blade upper surface*.—Very weak.
*Leaf blade tip*.—In the plane of the leaf.
*Undulation of margin*.—Slight.
*Thickness*.—Medium.
*Undulation of blade between main and lateral veins*.—Slight.
*Shape of teeth*.—Mixture of both sides straight and both sides convex.
*Length of teeth*.—Medium.
*Ratio length/width of teeth*.—Equal.
*Shape of upper lateral sinuses*.—Open.
*Depth of upper lateral sinuses*.—Medium.
*General shape petiole sinus*.—Wide open.
*Shape of base of upper leaf sinuses*.—U-shaped.
*Tooth at petiole sinus*.—Present on left side only.
*Density of prostrate hairs between veins on lower surface of blade*.—Absent.
*Density of erect hairs between veins on lower surface of blade*.—Absent.
*Density of prostrate hairs on main veins on lower surface of blade*.—None or very sparse.
*Density of erect hairs on main veins on lower surface of blade*.—Sparse.
*Density of prostrate hairs on main veins on upper surface of blade*.—Very sparse — sparse.
*Density of erect hairs on main veins on upper surface of blade*.—None.
*Autumn coloration of leaves*.—Leaves can be a single color or combination of colors, in a mottled pattern or on the edges of the leaves; Greyed purple; N186A, and B, and 187A, and B, and Greyed-red 181A, and C.

Upper surface:
*Color*.—Can be any of the following colors; Yellow-green to Green; 147A, and 137A, and B, and 146A.
*Anthocyanin coloration of main veins*.—Absent to very weak.

*Surface appearance*.—Dull.
*Blistering surface of blade*.—Absent to Very weak.

Lower surface:
*Color*.—Can be any of the following colors; Yellow green; 147A, and 137A, and B, and 146A.
*Anthocyanin coloration of main veins* (*lower surface*).—Absent to very weak.
*Glossiness*.—Weak.
*Surface texture*.—Smooth.
*Surface appearance*.—Dull.

Petiole:
*Length*.—About 11.5 cm.
*Length of petiole compared to middle vein*.—Slightly shorter.
*Density of prostrate hairs on petiole*.—None.
*Density of erect hairs on petiole*.—Sparse.

Buds:
*Bud fruitfulness*.—Basal: Mostly fruitful.
*Position of first fruitful shoot on previous season cane*.—$1^{st}$ to $2^{nd}$ node.
*Time of bud burst*.—Medium; Mar. 14, 2011.

FLOWERS

General:
*Flower sex*.—Hermaphrodite.
*Length of first inflorescence*.—Long; About 29.3 cm long by 6.4 cm wide.
*Position of first flowering and fruiting node*.—$3^{rd}$.
*Number of inflorescence per flowering shoot*.—1.1 to 2.
*Time of bloom*.—Midseason as compared with similar varieties in the growing area of Delano, Calif.
*Date of full bloom*.—May 20, 2011.

FRUIT

General:
*Ripening period*.—Early to Midseason; Approximately; Jul. 30, 2011.
*Use*.—Fresh market.
*Keeping quality*.—Excellent.
*Resistance to*.—Insects: Average typical of *Vitis vinifera* species. Diseases: Average typical of *Vitis vinifera* species.
*Refractometer test*.—Solid-sugar: About 20.6 Brix.
*Brix/acid*.—About 44.8.
*Titratable acidity*.—About 0.46.
*Juice pH*.—About 4.12.

Cluster:
*Mature cluster length* (*peduncle excluded*).—About 26.1 cm.
*Mature cluster width*.—About 12.3 cm.
*Mature cluster weight*.—About 478 g.
*Bunch density*.—Medium.
*Number of berries*.—About 204.
*Form*.—Cylindrical.

Peduncle:
*Lignification of peduncle*.—Medium.
*Length of peduncle*.—Medium. Approximately 4.2 cm.

Berry:
*Uniformity of size*.—Slightly variable.
*Single berry weight*.—About 4.4 g natural.
*Shape*.—Oblong.
*Seeds*.—Absent.
*Cross section*.—Circular.
*Berry dimensions*.—Longitudinal axis: About 40.2 mm. Horizontal axis: About 13.5 mm.
*Berry firmness*.—Medium.
*Particular flavor*.—Neutral.
*Bloom* (*cuticular wax*).—Weak.
*Berry separation from pedicel*.—Difficult.
*Skin color* (*without bloom*).—Can be either of the following colors; Greyed-Purple 187A, and B.

Skin:
*Thickness*.—Medium.
*Texture*.—Tender.
*Reticulation*.—Absent.
*Tenacity*.—Tenacious to flesh.

What is claimed:

1. A new and distinct variety of grapevine as herein illustrated and described.

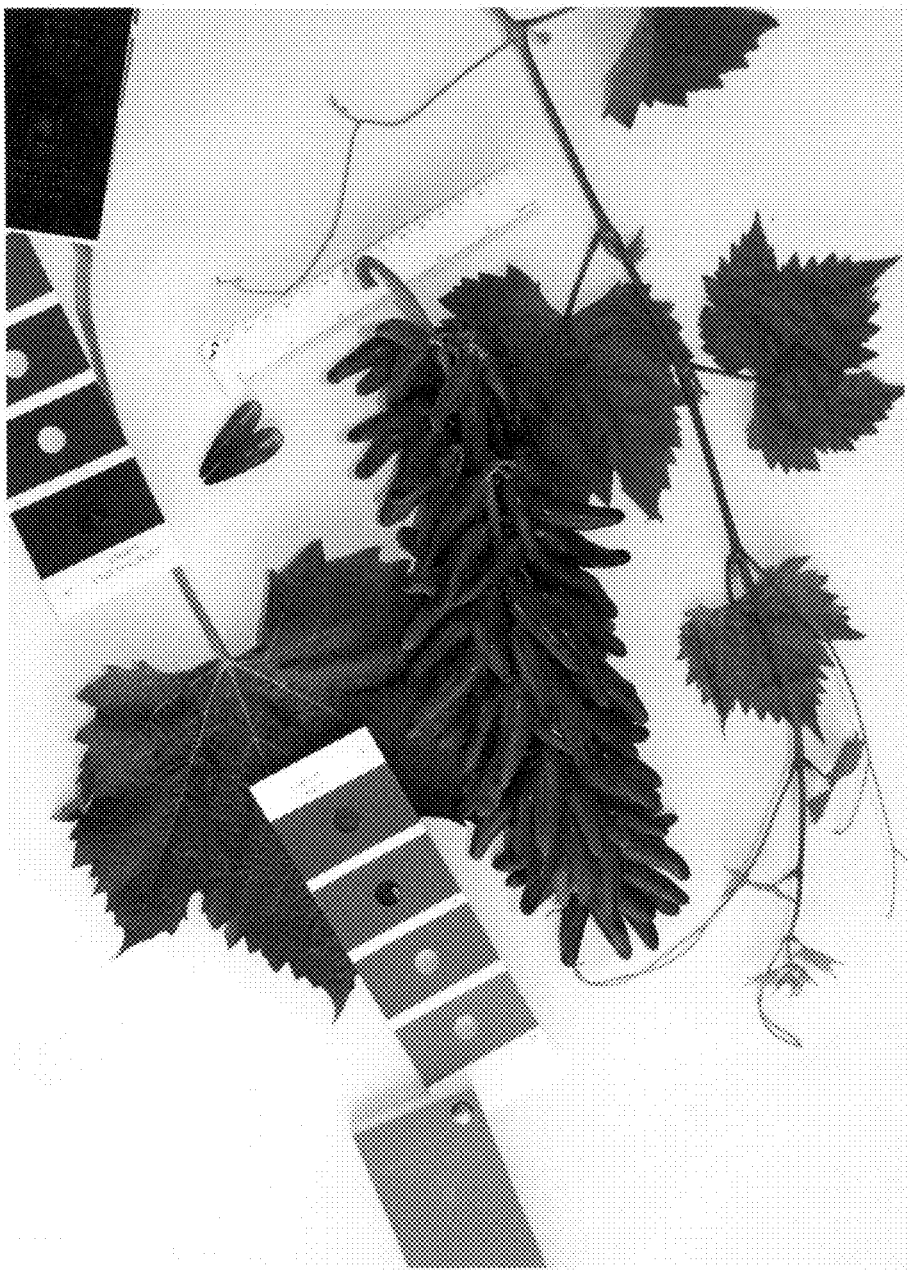

* * * * *